United States Patent

Cazeau et al.

Patent Number: 5,995,870
Date of Patent: Nov. 30, 1999

[54] MULTI-SITE CARDIAC STIMULATOR FOR THE TREATMENT OF CARDIAC INSUFFICIENCY BY STIMULATION

[75] Inventors: Serge Cazeau; Marcel Limousin, both of Paris; Philippe Ritter, Chatenay Malabry, all of France

[73] Assignee: ELA Medical S.A., Montrouge, France

[21] Appl. No.: 09/036,330

[22] Filed: Mar. 6, 1998

[30] Foreign Application Priority Data

Mar. 7, 1997 [FR] France ................................ 97 02754

[51] Int. Cl.⁶ .................................................. A61N 1/368
[52] U.S. Cl. .................................................. 607/9; 607/15
[58] Field of Search ................................ 607/9, 148, 15, 607/17, 18

[56] References Cited

U.S. PATENT DOCUMENTS

| | | | |
|---|---|---|---|
| 5,139,020 | 8/1992 | Koestner et al. | 128/419 |
| 5,174,289 | 12/1992 | Cohen | 128/419 |
| 5,179,949 | 1/1993 | Chirife | 607/9 |
| 5,584,868 | 12/1996 | Salo et al. | |
| 5,674,259 | 10/1997 | Gray | 607/20 |
| 5,720,768 | 2/1998 | Verboven-Nelissen | 607/9 |

FOREIGN PATENT DOCUMENTS 0522693  1/1993  European Pat. Off. ......... A61N 1/39

OTHER PUBLICATIONS

Schaldach, M.; "Pacemaker with PEP–Controlled Rate Adaptation", *Biomedizinische Technik*. vol. 34, No. 7/8, Jul. 1989, pp. 177–184.

*Primary Examiner*—Kennedy J. Schaetzle
*Attorney, Agent, or Firm*—Orrick, Herrington & Sutcliffe LLP

[57] ABSTRACT

A multi-site pulse generator for the treatment of cardiac insufficiencies by stimulation. In such a multi-site cardiac pulse generator, electrodes are placed in a plurality of distinct respective sites, including at least two ventricular sites. The electrodes are connected to independent outputs of the pulse generator in a manner that allows the detection of a potential of depolarization as well as the application of a stimulation pulse. A sensor of contraction of at least one of the ventricles is provided, to detect an instant of beginning of valvular opening, and a research system that determines an optimal electrode configuration operates to commute successively and automatically the different ventricular electrodes according to the various possible connection configurations, and to detect a depolarization or stimulation event on the electrode in the corresponding configuration; to determine a time interval separating, for each given configuration, the depolarization or stimulation event and the instant of beginning of the valvular opening, and to select therefrom the configuration obtaining the shortest time interval. The pulse generator also is able to apply a stimulation on the electrode in the selected optimal configuration, and automatically checks the configuration from time to time to maintain the optimal configuration from among the various configurations. The pulse generator may be included in a pacemaker, cardioverter or defibrillator, and may include single, double, triple or quadruple chamber modes.

20 Claims, 2 Drawing Sheets

MULTI-SITE CARDIAC STIMULATOR FOR THE TREATMENT OF CARDIAC INSUFFICIENCY BY STIMULATION

FIELD OF THE INVENTION

The present invention concerns cardiac pulse generators (or circuits for stimulation in a defibrillator or cardiovertor), and more particularly their utilization for the treatment of cardiac insufficiency by stimulation.

BACKGROUND OF THE INVENTION

In connection with the treatment of the cardiac rhythm disorder, different authors (Hochleitner, Bekker, Cazeau) have proposed to treat with the help of stimulation myocardial contraction disturbances observed in patients with cardiac insufficiency, which disturbances are spontaneous or induced by a traditional stimulation.

Indeed, one has observed that patients presenting class NYHA 3 and 4 disturbances could see their condition improved by an appropriate stimulation. It has been particularly proposed, in a first experience, to use a conventional double-chamber pacemaker by programming a short atrioventricular delay ("AVD"). In more recent studies, it has been proposed to stimulate right and left cavities in a triple chamber or quadruple chamber mode.

But, in all cases, no criterion of implantation has ever been clearly defined (except the criterion of a cardiac insufficiency). Nor has there been an explanation of the mechanisms implied in the correction of those cardiac disturbances. The programming of the different stimulation parameters is, therefore, in the current knowledge state, individualized for each patient and by each therapist.

OBJECTS AND SUMMARY OF THE INVENTION

It is an object of the present invention to palliate these limitations by proposing a pulse generator (also called a cardiac stimulator and a cardiac pulse generator (the terms being used interchangeably)) which is able to optimize stimulation parameters in an objective and predictable manner (that is to say, without the personal appreciation and involvement of the therapist), which is automatic, and preferably is adaptive over time according to the evolution, in the short term and in the long term, of the functional state of the patient.

The invention is based on the inventors' discovery that, for patients with implanted devices, echocardiographic examinations have shown that one optimizes the correction of the cardiac disturbance when the interval of time separating, on the one hand, the depolarization or the ventricular stimulation pulse, and, on the other hand, the beginning of the ventricular ejection, was the shortest possible. This interval corresponds in fact to the opening of sigmoïd valves (the pulmonary valve for the right ventricle and the aortic valve for the left ventricle), indicating the beginning of the systolic contraction phase, or ejection phase, that succeeds to the isovolumetric contraction phase of the corresponding ventricle.

The inventors also have observed that the interval in question is influenced by the choice of the site of the stimulation, that is to say, the interval is not the same depending on the chosen stimulation site in the ventricle.

Essentially, the invention proposes to use a pulse generator of the "multi-site" type and to foresee a means to test different possible sites and to choose the one site that gives the shortest possible time interval between the ventricular event (a delivered stimulation pulse or an evoked depolarization) and the beginning of the systole phase, and then to select and operate the therapeutic stimulation with this configuration.

A "multi-site" pacemaker is a known pacemaker type in which electrodes are placed in a plurality of distinct respective sites, with at least two ventricular sites (which at least two sites might be located in the same ventricle) and coupled to a multi-site pulse generator. It can concern a pacemaker of the "single chamber" type (double ventricular stimulation), double or triple chamber type (right atrial stimulation and double ventricular stimulation) or even quadruple chamber type (double atrial stimulation and double ventricular stimulation).

More precisely, the pacemaker embodiment of the invention, which is a pacemaker of the aforementioned "multi-site" type, that is to say in which electrodes are placed in a plurality of distinct respective sites comprising at least two ventricular sites, these electrodes being connected to independent outputs of the pulse generator of the pacemaker in a manner as to allow on each site the detection of a depolarization voltage potential, as well as the application of a stimulation pulse, is characterized by:

a contraction sensor responsive to at least one of ventricles, to detect an instant of the beginning of the valvular opening;

research means for determining the optimal electrode configuration, to commute successively and automatically the at least two ventricular electrodes according to the various possible configurations, and to detect a depolarization or stimulation event on the electrode in the corresponding configuration, to determine the time interval separating, for a given configuration, the depolarization or stimulation event and the instant of beginning of the valvular opening, and to select the configuration giving the shortest the time interval; and means to apply a stimulation on the electrode in the configuration selected by the research means.

The output of the pulse generator can thus be used during the research phase to deliver a stimulation pulse via the connected electrode to one of the distinct ventricular sites so that the time interval for the ventricular event of the one site and the following valvular opening can be separately measured to determine the optimal electrode confirguation.

According to various subsidiary advantageous characteristics, it also is foreseen in one embodiment to include means to detect atrial and ventricular extrasystoles, and to inhibit the research means in the case of a detection of an extrasystole.

In another embodiment, it is also foreseen to include a means to measure the value of the time interval determined for a given cardiac cycle, to compare the measured value to the corresponding measured value for a preceding cycle, and, in response to an increase of the aforementioned value, to cause the research means to determine again the optimal configuration.

It is a further embodiment to include means to determine a physiological rest state of the patient, and, when a state of rest is detected, to cause the research means to determine again the optimal configuration.

In yet another embodiment, the research means is put in action again at regular intervals, or after counting a predetermined number of cycles or on some other periodic or aperiodic basis, to provide for checking from time to time that the best site among the at least two ventricular sites is being used.

In addition, it is foreseen in an embodiment to include means to adapt or vary the delays between the sites of stimulation (stimulation events).

BRIEF DESCRIPTION OF THE DRAWINGS

Others characteristics and advantages of the invention will appear to a person of ordinary skill in the art in view of the following description of an example of an embodiment of the present invention, made with reference to the drawings annexed, in which.

DETAILED DESCRIPTION OF THE INVENTION

Figure 1:
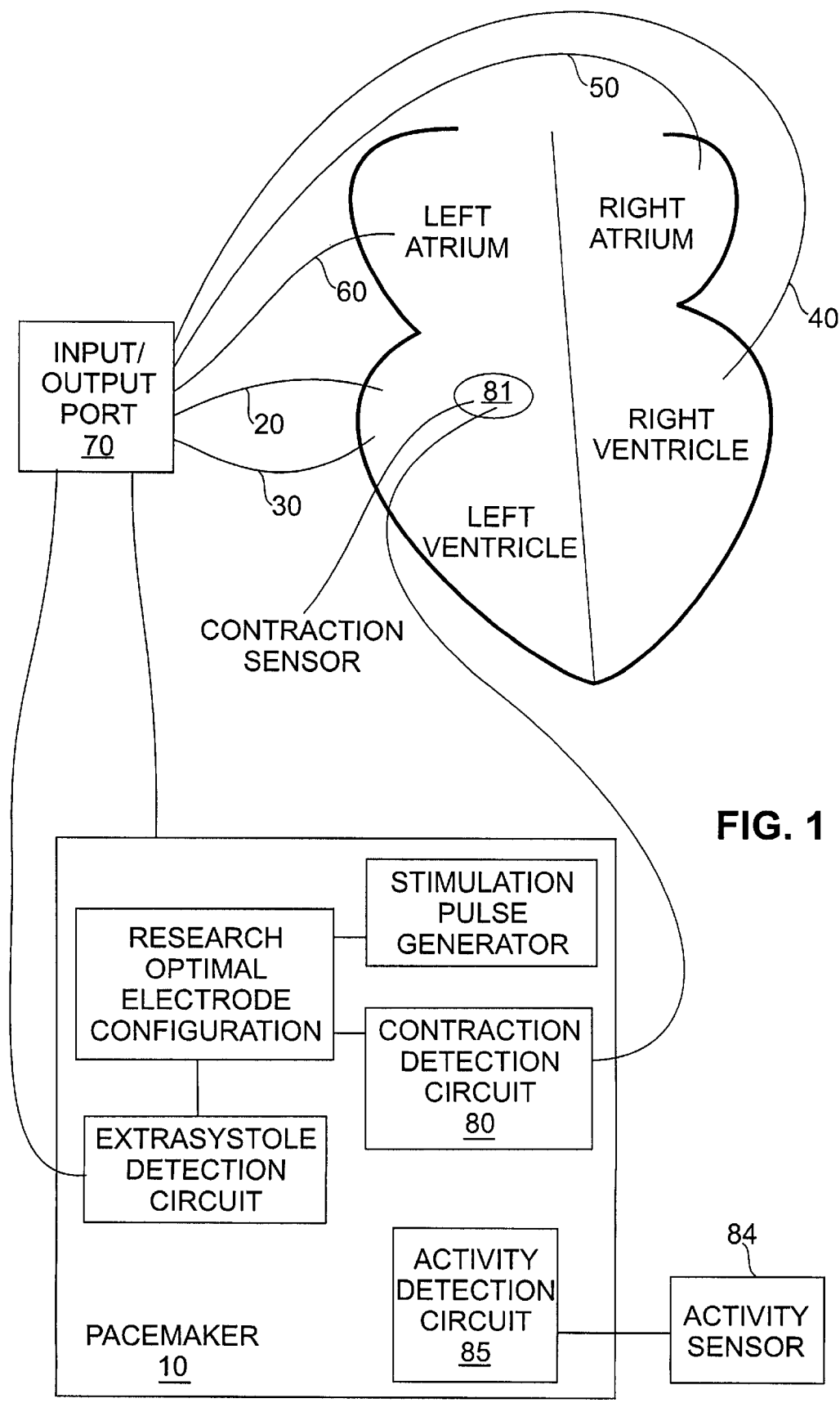
FIG. 1 is a schematic diagram of a quadruple chamber device in accordance with a preferred embodiment of the invention.

The term pacemaker as used herein is an implanted prosthesis (pacemaker, defibrillator or cardiovertor) having a pulse generator of the multi-site type, in which the different parameters, especially the configuration of stimulation sites, are chosen in a manner as to optimize the efficiency of the treatment of the cardiac insufficiency.

The pacemaker of the present invention is a pacemaker of a type itself well-known, that is to say a prosthesis for single or double chamber cardiac stimulation or cardiac defibrillation comprising at least two independent outputs for ventricular detection/stimulation, and a sensor of contraction of at least one of the ventricles, typically of the left ventricle. If the device is of the double, triple or quadruple chamber type, then it preferably also includes at least two independent outputs for atrial detection/stimulation.

The ventricular contraction sensor has for its object to determine the instant of opening of one of the two sigmoïd valves. This may be achieved by measuring variations of the volume, detecting the movement of ventricular muscular fibers in the beginning of a systole, or otherwise detecting the opening of a valve in a reliable manner. The instant of the opening of the valve corresponds to the transition between the isovolumetric contraction phase of the ventricle and the ejection phase of the aorta (for the left heart) or the pulmonary artery (for the right heart). This parameter can be determined by various known sensor types, such as a sensor that measures the electrical impedance of the myocardium, a sensor that measures the contractility of the ventricle, a sensor that measures the ventricular volume by magnetometry, a sensor that detects the opening of the valve by ultrasonic transducer, light, color, etc. One suitable sensor which may be situated on a stimulation probe (lead) for the detection of the opening of valves are described in the U.S. Pat. No. 5,243,976. One suitable sensor for the measure of the contractility is described in the U.S. Pat. No. 5,154,171. These patents are herein incorporated by reference.

One can thus apply a stimulation to at least several ventricular sites, on the left ventricle or the right ventricle, or a plurality of sites on the left and/or right ventricle, etc.

To determine the site(s) of optimal stimulation, a research phase is performed in which one stimulates the ventricle or ventricles with each of the different possible configurations by adapting delays between each stimulation site, and measuring each time the interval of time separating the stimulation (or the beginning of the evoked depolarization) of the ventricle on the one hand, and the instant (or beginning) of the valvular opening (as defined above) on the other hand, and determining which site is the configuration that obtains the shortest time interval from depolarization to beginning of valvular opening. This last value, that is the shortest time interval, is memorized (stored in memory) as constituting the optimal value. The device applies thereafter a controlled stimulation with the configuration of electrodes thus selected. The time between a spontaneous depolarization and valvular opening also might be used.

One will be able then to control, while remaining in this configuration, the other parameters of functioning of the pacemaker, such as the atrio-ventricular delay, left ventricle-right ventricle delay, etc.

According to another aspect of the invention, after the research phase that was just described, which allowed the device to select the optimal configuration, the pacemaker insures a follow-up of this selection so as to verify whether the configuration is found always to be the optimal configuration. This follow-up is operated by measuring, at each cardiac cycle or at regular intervals, the delay interval from the depolarization to the beginning of the valvular opening, and comparing the measured delay interval to the time interval that had been memorized as the optimal value during the last research phase. If this interval has increased, one can suppose that the configuration is no longer optimal and one executes again a research phase as previously described. Alternately, or in addition, if every measured cycle is compared to a prior measured value (or an average of such prior measured values) one can thus consider that every cycle whose interval in question is greater than the preceding cycle interval increased by a given programmable percentage (typically of a percentage of 6.25 to 50%) will be revealing of a possible mis-adaptation of the chosen electrode configuration, which then will lead to a new determination of the configuration optimization.

One will note that, to allow a satisfactory functioning, one can eliminate from the analysis all cycles presenting an anomaly, especially atrial extrasystoles and ventricular extrasystoles (that is, a ventricular detection not preceded by an atrial depolarization). One will advantageously refer, for the definition of the ventricular extrasystoles, to FR-A-2 675 695 and to EP-A-0 550 342 (and its corresponding U.S. Pat. No. 5,312,451, which is incorporated herein by reference). One also will refer to FR-A-2 680 093 and its corresponding U.S. Pat. No. 5,411,533 (which also is incorporated herein by reference) for a discussion of capture of the evoked depolarzation.

According to another aspect of the invention, the pacemaker is able to discriminate between a phase of rest and a phase of activity of the patient, for example, by an analysis of signals delivered by a minute-ventilation (also known as minute volume) sensor. Such a discrimination between periods of activity and rest is previously described in EP-A-0 719 568 and its corresponding U.S. Pat. No. 5,622,428 which is incorporated herein by reference. If, during of a phase of rest, the time interval between the depolarization and the beginning of ejection has not returned to the optimal value that had been memorized in the course of the research phase at the initialization, for example, after a programmable number of consecutive sinus cycles (typically a programmable number between 1 to 100), the research phase is then executed again as described above. If the pacemaker finds a new configuration with an interval between depolarization and beginning of ejection that is shorter, it then selects this configuration and replaces the value memorized at the initialization with the new shorter value. In the opposite case, it preserves the present configuration, and updates the memorized value of the time interval between the depolarization and the beginning of ejection as optimal with the last measured value at rest.

Referring to FIG. 1, an embodiment of the present invention is illustrated as a pacemaker 10 of a quadruple chamber type itself well-known, that is to say a prosthesis for double chamber cardiac stimulation (or cardiac defibrillation) comprising two independent leads 20 and 30 for left ventricular detection/stimulation, one independent lead 40 for right ventricular detection/stimulation, and leads 50 and 60 for left and right atrial detection/stimulation respectively. These leads are connected to independent inputs/outputs of input/output port 70 of pacemaker 10. It should be understood that port 70 is shown separated from pacemaker 10 only for illustrative purposes. Pacemaker 10 also includes a contraction sensor 81 and a contraction detection circuit 80 coupled to at least one of the ventricles, typically the left ventricle, as illustrated.

The ventricular contraction sensor 81 is used to determine the instant of opening of one of the two sigmoid valves in this embodiment by detecting the movement of ventricular muscular fibers in the beginning of a systole. An activity sensor 84 and activity detection circuit 85 also are provided to indicate when the patient is and is not in a rest condition.

Figure 2:
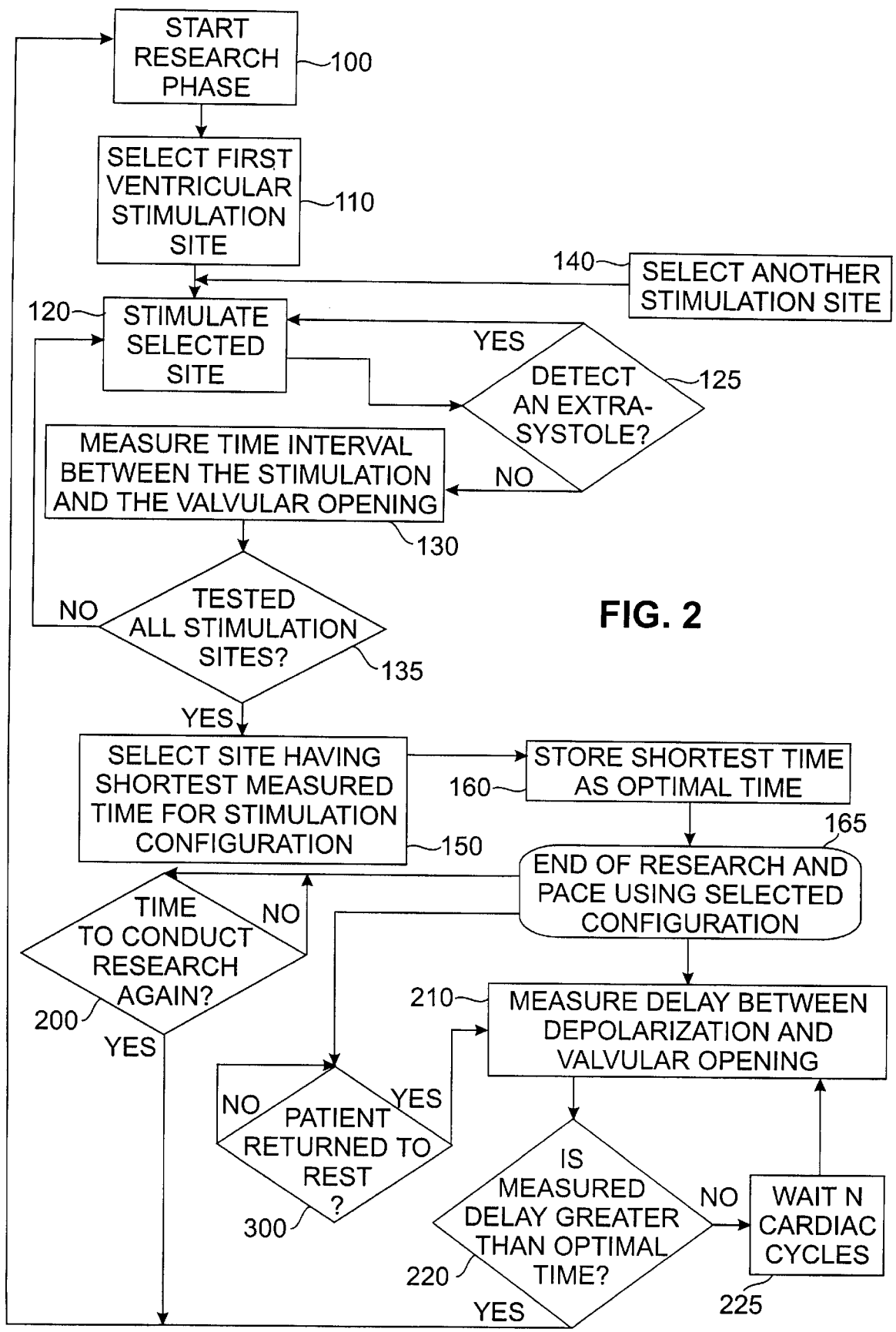
FIG. 2 is a flow chart of a process for selecting a stimulation configuration in accordance with a preferred embodiment of the present invention.

With reference to FIG. 2., to determine the site(s) of optimal stimulation, a research phase is performed at step 100 in which one selects at step 110 and stimulates at step 120 one of the ventricles with each of the different possible configurations, and measures each time the interval of time separating the stimulation (or the beginning of the evoked depolarization) of the ventricle on the one hand, and the instant (or the beginning) of the valvular opening on the other hand, at step 130, repeating the sequence until all sites have been studied (steps 135, 140) and then determining at step 150 which site is the configuration that obtains the shortest interval from depolarization to beginning of valvular opening. This last value, that is the shortest time interval, is memorized (stored in memory) at step 160 as the optimal value. The research phase is then complete and the device applies thereafter a controlled stimulation (pace) with the configuration of electrodes thus selected as providing the shortest time at step 165.

After the research phase is complete at step 165, the pacemaker performs a follow-up of this selection at steps 200 and 210 so as to verify whether the last selected configuration is still the optimal configuration. This follow-up is operated at step 210 by measuring, at each cardiac cycle or at regular intervals, e.g., N cardiac cycles (step 225), the delay interval from the depolarization to the beginning of the valvular opening, and at step 220 comparing the measured delay interval to the time interval that had been memorized as the optimal value during the last research phase at step 160. If this interval has increased, one can suppose that the configuration is no longer optimal and one executes again a research phase beginning at step 100, as previously described. Alternately, or in addition, if every measured cycle is compared to a prior measured value (or an average of such prior measured values) (steps 225, 210) one can thus consider that every cycle whose interval in question is greater than the preceding cycle interval increased by a given programmable percentage (typically of a percentage of 6.25 to 50%) will be revealing of a possible mis-adaption of the chosen electrode configuration, which then will lead to a new determination of the configuration optimization beginning at step 100.

One will note that, to allow a satisfactory functioning, one can eliminate from the analysis all cycles presenting an anomaly, especially atrial extrasystoles and ventricular extrasystoles (that is, a ventricular detection not preceded by an atrial depolarization) as detected at step 125.

Optionally, the pacemaker is able to discriminate at step 300 between a phase of rest and a phase of activity for the patient, for example, by an analysis of signals delivered by an activity sensor 84 and an activity detection circuit 85 such as a minute-ventilation (also known as minute volume) sensor. If, during a phase of rest, the time interval between the depolarization and the beginning of ejection has not returned to the optimal value that had been memorized in the course of the research phase at the initialization (step 220), for example, after a programmable number N of consecutive sinus cycles (typically a programmable number between 1 to 100) (step 225), the research phase is then executed again at step 100 as described above.

One skilled in the art will appreciate that the present invention can be practiced by other than the described embodiments, which are presented for purposes of illustration and not of limitation.

We claim:

1. A multi-site cardiac pulse generator, in which electrodes are placed in a plurality of distinct respective sites comprising at least two ventricular sites, these electrodes being connected to independent outputs of the pulse generator in a manner to allow the detection of a potential of depolarization as well as an application of a stimulation pulse, comprising:

a sensor of contraction of at least one of the ventricles, to detect an instant of beginning of the valvular opening; and research means for determining an optimal electrode configuration, adapted to:

commute successively and automatically the at least two ventricular electrodes according to a number of various possible configurations, detect a ventricular event on the commuted electrode in the corresponding configuration, determine the time interval separating, for a given electrode configuration, the detected ventricular event from the detected instant of the beginning of the valvular opening, and select the configuration that gives the shortest time interval; and means for applying a stimulation pulse on the electrode in the configuration selected by the research means.

2. The pulse generator of claim 1, comprising means for detecting an extrasystole, and means for inhibiting the research means from determining in response to a detected extrasystole.

3. The pulse generator of claim 2, wherein the means for detecting an extrasystole further comprises means for determining an atrial extrasystole and a ventricular extrasystole.

4. The pulse generator of claim 1, wherein the research means further comprises a memory and means for memorizing a measured shortest time interval for the selected configuration and further comprising:

means for determining a time interval for a given cardiac cycle;

means for comparing the determined time interval determined for the given cardiac cycle to the corresponding shortest time interval memorized at a preceding cardiac cycle, and means for putting in action the research means in response to the determined time interval being greater than the memorized shortest time interval.

5. The pulse generator of claim 1, wherein the preceding cardiac cycle further comprises the cardiac cycle of the last selection of the optimal configuration by said research means.

6. The pulse generator of claim 1, further comprising:
means for determining a physiological rest state of the patient, and means for putting again in action the research means in response to a detected state of rest.

7. The pulse generator of claim 1, further comprising means for putting the research means in action at regular intervals.

8. The pulse generator of claim 1 further comprising means for counting a predetermined number of cardiac cycles, and means for putting the research means in action regularly after counting of the predetermined number of cycles.

9. The pulse generator of claim 1, further comprising means to adapt delays between sites of stimulation.

10. A process for configuring a multi-site cardiac pulse generator having electrodes placed on at least two distinct ventricular sites, the electrodes being respectively connected to an independent output of the pulse generator in a manner to allow the detection of a ventricular event as well as an application of a stimulation pulse, comprising:
   (a) connecting one of the ventricular electrodes to the generator output.
   (b) detecting a ventricular event on said connected electrode selected from among a depolarization and a stimulation;
   (c) detecting an instant of beginning of the valvular opening of at least one of the ventricles following said detected ventricular event;
   (d) determining a time interval separating the detected ventricular event from the detected instant of the beginning of the valvular opening;
   (e) repeating steps (a)–(d) for each ventricular electrode connected to a distinct ventricular site;
   (f) identifying the determined time interval that is the shortest time interval for the given configurations; and
   (g) selecting the electrode configuration that gives the shortest time interval for applying a stimulation pulse.

11. The method of claim 10, wherein step (b) further comprises detecting an extrasystole, and inhibiting steps (a)–(d) for a given cycle in response to a detected extrasystole.

12. The method of claim 11, further comprising:
storing the determined shortest time interval for the selected configuration;

determining a value for a cardiac cycle of the time interval between a ventricular event and a valvular opening;

comparing the determined value of the time interval determined for the given cardiac cycle to the stored determined shortest time interval, and performing steps a)–f) again in response to the time interval detected being greater than the stored time interval.

13. A multisite cardiac pulse generator, having electrodes adapted to be connected to at least two distinct ventricular sites and a sensor of contractions, adapted to be configured according to the method of claim 12.

14. The method of claim 10, wherein detecting an extrasystole further comprises detecting atrial and ventricular extrasystoles.

15. The method of claim 10, further comprising:
   (h) determining a physiological rest state of the patient, and
   (i) repeating steps a)–f) in response to a detected state of rest.

16. A multisite cardiac pulse generator, having electrodes connected to at least two distinct ventricular sites and a sensor of contraction, adapted to be configured according to the method of claim 15.

17. The method of claim 10, further comprising
   (h) repeating steps a)–f) at regular intervals.

18. The method of claim 10, further comprising
   (h) counting a predetermined number of cardiac cycles, and
   (i) repeating steps a)–f) regularly after counting the predetermined number of cycles.

19. The method of claim 10, further comprising adapting delays between sites of stimulation.

20. A multisite cardiac pulse generator, having electrodes adapted to be connected to at least two distinct ventricular sites and a sensor of contraction, adapted to be configured according to the methods of claim 10.

* * * * *